United States Patent [19]

O'Lenick, Jr.

[11] Patent Number: 5,093,452
[45] Date of Patent: Mar. 3, 1992

[54] SILICONE PHOSPHATE AMINES

[75] Inventor: Anthony J. O'Lenick, Jr., Lilburn, Ga.

[73] Assignee: Siltech Inc., Norcross, Ga.

[21] Appl. No.: 756,790

[22] Filed: Sep. 9, 1991

Related U.S. Application Data

[63] Continuation-in-part of Ser. No. 546,358, Jun. 27, 1990, Pat. No. 5,070,171.

[51] Int. Cl.$^5$ ............................................. C08G 77/04
[52] U.S. Cl. ..................................... 528/25; 525/474; 528/33; 556/405; 556/413; 556/419; 556/425; 427/387
[58] Field of Search .............................. 528/28, 25, 33; 525/474; 556/405, 419, 413, 425; 427/387

[56] References Cited

U.S. PATENT DOCUMENTS 4,370,255  1/1983  Plueddemann ..................... 556/405
4,640,790  2/1987  Sylvester et al. ................... 556/405

Primary Examiner—Melvyn I. Marquis

[57] ABSTRACT

The present invention relates to a series of novel silicone phosphate organic amine salts. These compounds have one or more pendant phosphate group in the free acid form which is neutralized by a fatty amine group. The amine group will become protonated and a net positive charge will result. The phosphate will donate the proton and develop a net negative charge. This compound is more substantive and higher foaming than any of the components alone. These phosphated silicone salts by virtue of this unique salt formation is highly foaming, non irritating to eyes and skin and deposits on fiber surfaces and form effective surface modifying finishes. The compounds of the present invention are therefore very well suited to applications in the personal care market.

18 Claims, No Drawings

SILICONE PHOSPHATE AMINES

RELATED APPLICATIONS

This application is a continuation in part of copending application Ser. No. 07/546,358 filed 06/27/1990 now U.S. Pat. No. 4,070,171.

BACKGROUND OF THE INVENTION

1. Field of Invention

The present invention relates to a series of novel silicone phosphate salts of organic amines which are high foaming low irritation surface active agents that are substantive to fiber and hair. The compounds, because they contain both a pendant ionizable phosphate group and are the salt of an organic amine the compounds have unique solubility in a variety of solvents. The compounds of the present invention are high molecular weight silicone polymers, they have a high degree of oxidative stability, even at elevated temperatures and are nonirritating to skin and eyes. In addition, these compounds are non volatile and exhibit a inverse cloud point. These combination of properties makes these polymers ideally suited for use in personal care applications.

The compounds of the present invention are based upon raw materials which are prepared by the phosphation of a pendant hydroxyl group which is present on a silicone polymer. The phosphated silicone polymers are subject of a copending application upon which this is a continuation in part.

The technology used to produce the compounds of the present invention is very flexible and allows us to prepare performance tailored molecules for specific applications.

2. Description of the Arts and Practices

Silicone oils (dimethylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicon dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not ionically bonded the effect is very transient. The product is removed with one washing.

Silicone phosphates are the basic raw material used for the preparation of the compounds of the present invention. The current application is a continuation in part of the copending patent application which discloses how to make the silicone phosphates. It was also not until the compounds of the present invention that the concept and technology needed to incorporate silicone into the amine salt was created. The beneficial effects of the lowering irritation, providing increased substantivity to both hair and skin and antistatic properties were never anticipated by the references

THE INVENTION

Object of the Invention

It is the object of the present invention to provide a series of novel silicone phosphate organic amine salts which are high foaming, low irritation to eyes and skin, have an inverse cloud point and are substantive to the surface of a fibers.

Still another object of the present invention is to provide a series of products having differing solubilities in water and organic solvents. This is achieved by selection of the phosphated silicone polymer used as a raw material and the amine chosen for preparation of the salt.

Application of the compounds of the invention can be from solvent, aqueous dispersion or solution, or applied heat in these processes.

The phosphated silicone polymers, suitable as raw materials, in a preferred embodiment, contain varying amounts of ethylene oxide, propyleen oxide or butylene oxide or mixtures thereof. The presence of the oxide in the phosphated silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to skin, hair and fiber.

In another preferred embodiment a is an integer from 10 to 100; b is an interger from 10 to 100; and c is an integer from 5 to 20.

In still another preferred embodiment x, y and z are independently integers ranging from 1 to 10.

SUMMARY OF THE INVENTION

The present invention relates to a series of novel silicone phosphate organic amine salts. These compounds have one or more pendant phosphate group in the free acid form which is neutralized by a fatty amine group. The amine group will become protonated and a net positive charge will result. The phosphate will donate the proton and develop a net negative charge. This compound is more substantive and higher foaming than any of the components alone,. These phosphated silicone salts by virtue of this unique salt formation is highly foaming, non irritating to eyes and skin and deposits on fiber surfaces and form effective surface modifying finishes. The compounds of the present invention are therefore very well suited to applications int he personal care market.

The compounds of this invention having a pendant group represented by the following formula:

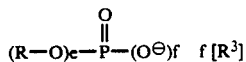

wherein
R is

R is

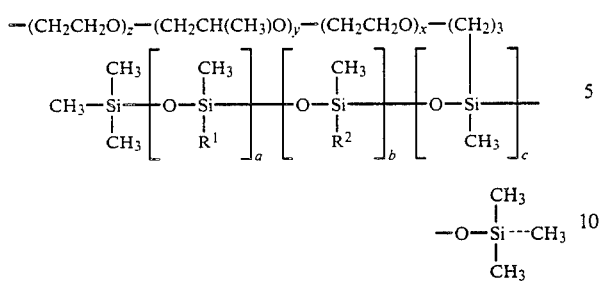

a is an integer from 0 to 200;
b is an integer from 0 to 200;
c is an integer from 1 to 200;
$R^1$ is selected from $-(CH_2)_nCH_3$ and phenyl;
n is an integer from 0 to 10;
$R^2$ is $-(CH_2)_3-(OCH_2CH_2)_x-(OCH_2CH(CH_3))_y-(OCH_2CH_2)_z-OH$;
x, y and z are integers and are independently selected from 0 to 20;
e and f range from 1 to 2 with the proviso that e+f=3;
$R^3$ is selected from

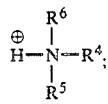

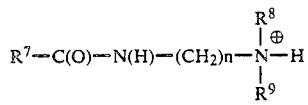

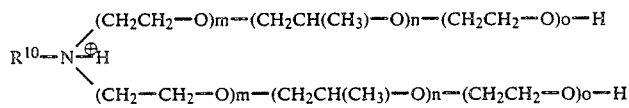

or

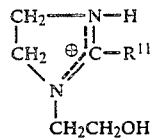

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are independently selected from lower alkyl having from one to three carbon atoms;
$R^{10}$ is alkyl having from 6 to 20 carbon atoms;
$R^{11}$ is alkyl having from 6 to 20 carbon atoms;
m, n and o are independently integers each ranging from 0 to 20.

The reaction sequence needed to produce the compounds of the present invention starts with a silicone phosphate of the following structure;

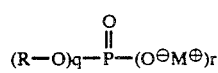

wherein

R is

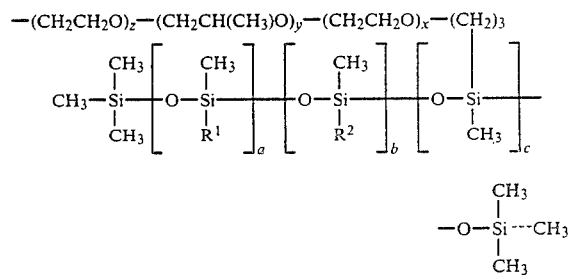

a is an integer from 0 to 200;
b is an integer from 0 to 200;
c is an integer from 1 to 200;
$R^1$ is selected from $-(CH_2)_nCH_3$ or phenyl;
n is an integer from 0 to 10;
$R^2$ is $-(CH_2)_3-(OCH_2CH_2)_x-(OCH_2CH(CH_3))_y-(OCH_2CH_2)_z-OH$;
x, y and z are integers and are independently selected from 0 to 20;
q and r range from 1 to 2 with the proviso that q+r=3;

M is H.

These materials are items of commerce available from Siltech Inc. Norcross Ga.

The reactive intermediates are prepared by the neutralization reaction of the silicone phosphate with an equivalent of the organic amine specified. The neutralization may be carried out either neat or in a suitable solvent like water.

PREFERRED EMBODIMENT

In one embodiment the tertiary amine is an tri alkyl amine conforming to the following structure;

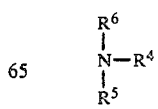

$R^4$ is alkyl having from 1 to 20 carbon atoms;

$R^5$ is alkyl having from 1 to 20 carbon atoms;
$R^6$ is alkyl having from 1 to 20 carbon atoms;

In a preferred embodiment the tertiary amine reacted with the silicone phosphate intermediate is an N alkyl amido, N dialkyl amine,

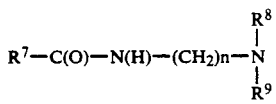

$R^7$ is alkyl having from 1 to 20 carbon atoms;
$R^8$ and $R^9$ are independently selected from lower alkyl having from one to three carbon atoms.

In an another preferred embodiment the tertiary amine reacted with the silicone phosphate intermediate is an imidazoline.

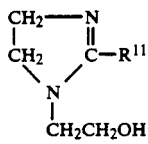

$R^{11}$ is alkyl having from 6 to 20 carbon atoms.

In still another preferred embodiment the tertiary amine reacted with the silicone phosphate intermediate is an alkoxyethyl alkyl amine conforming to the following structure;

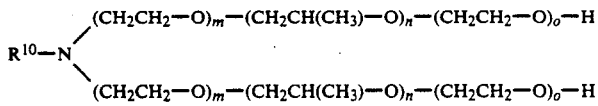

$R^{10}$ is alkyl having from 6 to 20 carbon atoms;
m, n, and o are independently integers each ranging from 0 to 20.

The present invention discloses a process for conditioning fibers which comprises contacting the fiber with an effective conditioning amount of a silicone phosphate compound which conforms to the following structure;

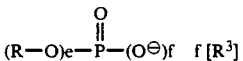

wherein
R is

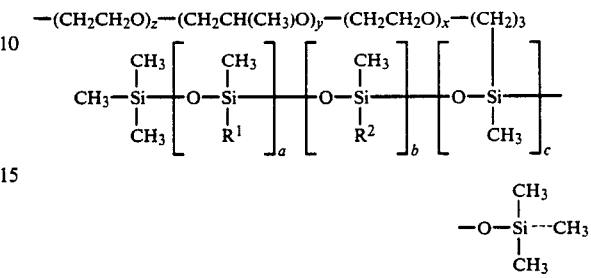

a is an integer from 0 to 200;
b is an integer from 0 to 200;
c is an integer from 1 to 200;
$R^1$ is selected from $-(CH_2)_nCH_3$ or phenyl;
n is an integer from 0 to 10;
$R^2$ is $-(CH_2)_3-(OCH_2CH_2)x-(OCH_1CH(CH_3))y-(OCH_2CH_2)z-OH$;
x, y and z are integers and are independently selected from 0 to 20;
e and f range from 1 to 2 with the proviso that $e + f = 3$;
$R^3$ is selected from

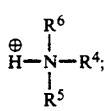

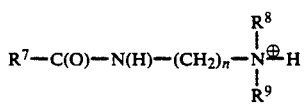

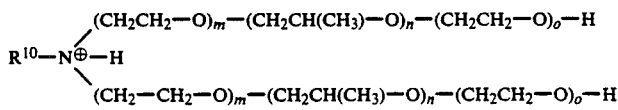

or

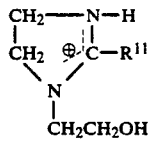

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are lower alkyl having from one to three carbon atoms;

$R^{10}$ is alkyl having from 6 to 20 carbon atoms;
$R^{11}$ is alkyl having from 6 to 20 carbon atoms;
m, n and o are independently integers each ranging from 0 to 20.

In a preferred embodiment the process utilizes a compound conforming to the following structure;
$R^3$ is

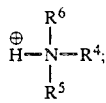

$R^4$ is alkyl having from 1 to 20 carbon atoms;
$R^5$ is alkyl having from 1 to 20 carbon atoms;
$R^6$ is alkyl having from 6 to 20 carbon atoms;

In another preferred embodiment the process makes use of a compound of the following structure;
$R^3$ is

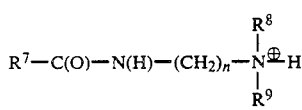

$R^7$ is alkyl having from 6 to 20 carbon atoms;
$R^8$ is alkyl having from 1 to 20 carbon atoms;
$R^9$ is alkyl having from 1 to 20 carbon atoms;

In still another preferred embodiment the process makes use of the compound wherein;
$R^3$ is

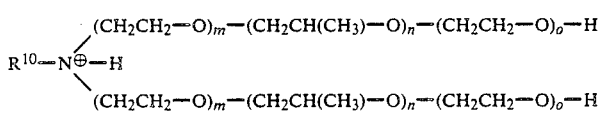

$R^{10}$ is alkyl having from 6 to 20 carbon atoms;
m, n, and o are independently integers each ranging from 0 to 20.

In another preferred embodiment the process utilizes a compound conforming to the following structure;
$R^3$ is

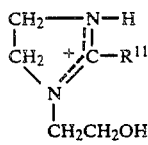

$R^{11}$ is alkyl having from 6 to 20 carbon atoms.

The effective conditioning amount of compound ranges from 0.1 to 50% by weight. and in a preferred embodiment the effective conditioning amount ranges from 1.0 to 5.0% by weight.

EXAMPLES

Dimethicone Copolyols

The phosphate esters used as raw materials for the preparation of the compounds of the present invention are prepared by reaction of a hydroxyl containing silicone polymer with a suitable phosphating reagent.

One method of placing preparing the reactive hydroxyl containing silicone polymer is to react silanic hydrogen containing polymer with allyl alcohol or allyl alcohol alkoxylate monomer. Procedures this reaction are well known to those skilled in the art. U.S. Pat. No. 4,083,856 describe suitable processes.

EXAMPLES

Vinyl Intermediate Compounds

Compounds of this call are prepared by alkoxylation of allyl alcohol using methods well known to those skilled in the art. The following are some of the many compounds which can be used to make the products of this invention.

| $CH_2=CH-CH_2-O-(CH_2-CH_2-O)$ $x-(CH_2-CH(CH_3)-O)y-(CH_2-CH_2-O)z-H$ | | | | |
|---|---|---|---|---|
| Designation | x | y | z | Molecular Weight |
| A | 3 | 0 | 0 | 189 |
| B | 9 | 27 | 3 | 2,178 |
| C | 11 | 3 | 0 | 718 |
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (*Silicone Alkylene Oxide Copolymers As Foam Control Agents*) WO 86/0541 by Paul Austin (Sept. 25, 1986) p. 16 (examples 1 to 6) teaches how to make the following intermediates, and is incorporated herein by reference.

Hydrosilation of Intermediates

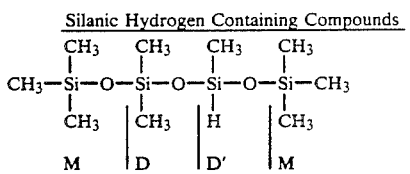

Silanic Hydrogen Containing Compounds

Group Designations

| Example | Austin Example | Group Designation | Average Molecular Weight | Equivalent Molecular Weight |
|---|---|---|---|---|
| 1 | 1 | $MD_{20} D'_{3.2}M$ | 1,850 | 551 |
| 2 | 4 | $MD_{160} D'_5M$ | 24,158 | 4,831 |
| 3 | 6 | $MD_{20} D'_{10}M$ | 2,258 | 225 |

Hydrosilation Compounds

The hydrosilation reaction used to make the compounds of this invention are well known to those skilled in the art. Reference; International Publication (*Silicone Alkylene Oxide Copolymers As Foam Control Agents*) WO 86/0541 by Paul Austin (Sept. 25, 1986) p. 19.

EXAMPLE 4

To a 22 liter three necked round bottom flask fitted with a mechanical agitator, thermometer with a Thermo-watch temperature regulator, nitrogen sparge tube vented reflux condenser and heating mantle is added 189.0 grams of Vinyl Intermediate Example #A. Next add 225 grams of Silanic Hydrogen Containing Compound Example #3 and 3,000 grams of toluene. Heat to 115° C. to remove azeotropically remove any water and 200 ml of toluene. The temperature is reduced to 85° C. and 3.5 ml of 3% $H_2PtCl_6$ in ethanol is added. Light to then excluded from the flask by covering it with a black cloth. An exotherm is noted to about 95° C. while the contents are stirred for about 2 hours. During this time silanic hydrogen concentration drops to nil. Cool to 65° C. and slowly add 60 g of sodium bicarbonate. allow to mix overnight and filter through a 4 micron pad. Distill off any toluene at 100° C. and 1 torr.

EXAMPLE 5-10

The above procedure is repeated, only this time replacing both the silanic hydrogen compound #3 with the specified number of grams of the specified silanic hydrogen compound and the vinyl intermediate example A with the specified number of grams of the specified vinyl intermediate.

| | Vinyl Intermediate | | Silanic Hydrogen Compound | |
|---|---|---|---|---|
| Example | Example | Grams | Example | Grams |
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

PHOSPHATION

Phosating Agents

Polyphosphoric Acid (PPA) is 115% phosphoric acid. When used as a phosphating agent in gives more mono ester than the phosphorus pentoxide. Phosphorus pentoxide is $P_2O_5$. It is more aggressive in phosphation and results in more diester.

The silicone phosphate of this invention can be prepared by reacting the hydroxyl containing silicon polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

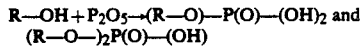

It will be understood by the above reaction that the product of phosphation, weather using polyphosphoric acid or phosphorus pentoxide give a mixture of mono and di ester.

The following examples further illustrate the objects and advantages of this invention, though it should be understood that the various reactants and amounts thereof, reaction conditions, and other details are merely illustrative and should not be construed to unduly limit this invention.

GENERAL PROCEDURE

The preparation of the phosphate of the current invention requires several steps. These steps in order are (a) phosphation, (b) dilution in water and neutralization with the amine. It is advantageous to run these reactions in the same reaction vessel, one process right after the other. This "tandem type reaction" sequence is preferred, but not required. Examples given here employ the tandem reaction technique.

(a) Phosphation

The specified amount of hydroxy silicone compound (Examples 4-10) is added to a suitable vessel. The specified amount of either polyphosphoric acid or phosphorus pentoxide is charged to under good agitation over a 2 hr. period. The exothermic reaction raises the temperature of the mixture to about 70° C. After 1 hour slowly raises the temperature to 100° C. and hold 2-4 hours.

| | Hydroxy Silicone | | Polyphosphoric Acid |
|---|---|---|---|
| Example | Example | Grams | Grams |
| 11 | 4 | 740.0 | 56.5 |
| 12 | 5 | 7009.0 | 56.5 |
| 13 | 6 | 943.0 | 56.5 |
| 14 | 7 | 608.0 | 56.5 |
| 15 | 8 | 7771.0 | 56.5 |
| 16 | 9 | 1105.0 | 56.5 |
| 17 | 10 | 2021.0 | 56.5 |

| | Phosphorus Pentoxide | | |
|---|---|---|---|
| | Hydroxy Silicone | | Phosphorus Pentoxide |
| Example | Example | Grams | Grams |
| 18 | 11 | 798.0 | 36.0 |
| 19 | 12 | 7067.0 | 36.0 |
| 20 | 13 | 1001.0 | 36.0 |
| 21 | 14 | 666.0 | 36.0 |
| 22 | 15 | 7829.0 | 36.0 |
| 23 | 16 | 1163.0 | 36.0 |
| 24 | 17 | 2079.0 | 36.0 |

Raw Material Amines

Class 1

Alkyl Tertiary amines

$R^1$ is alkyl having from 1 to 20 carbon atoms;
$R^5$ is alkyl having from 1 to 20 carbon atoms;
$R^6$ is alkyl having from 1 to 20 carbon atoms;

| Raw Material Example | $R^4$ | $R^5$ | $R^6$ | Molecular Weight |
|---|---|---|---|---|
| A | CH3 | C12H25 | CH3 | 213.0 |
| B | C2H5 | C6H13 | C2H5 | 143.0 |
| C | CH3 | C8H17 | CH3 | 143.0 |
| D | CH3 | C10H21 | CH3 | 171.0 |
| E | CH3 | C18H37 | CH3 | 283.0 |
| F | CH3 | C20H41 | CH3 | 311.0 |
| G | C6H13 | C6H13 | CH3 | 185.0 |
| H | CH3 | C10H21 | C10H21 | 297.0 |

Class 2

Alkyl amido Amines

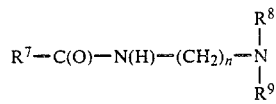

$R^1$ is alkyl having from 1 to 20 carbon atoms;
$R^8$ and $R^9$ are independently selected from lower alkyl having from one to three carbon atoms.

| Raw Material Example | $R^7$ | $R^8$ | $R^9$ | Molecular Weight |
|---|---|---|---|---|
| I | C7H15 | CH3 | CH3 | 129.0 |
| J | C11H23 | CH3 | CH3 | 185.0 |
| K | C13H27 | CH3 | CH3 | 213.0 |
| L | C17H35 | CH3 | CH3 | 269.0 |
| M | C19H39 | C2H5 | C2H5 | 325.0 |
| N | C6H13 | C2H5 | C2H5 | 143.0 |
| O | C20H21 | C2H5 | C2H5 | 319.0 |
| P | C11H23 | C2H5 | C2H5 | 213.0 |

Class 3

Alkyl alkoxy amines

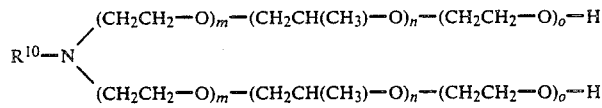

$R^{10}$ is alkyl having 6 to 20 carbon atoms;
m, n, and o are independently integers each ranging from 0 to 20.

| Raw Material Example | $R^{10}$ | m | n | o | Molecular Weight |
|---|---|---|---|---|---|
| Q | C6H13 | 20 | 20 | 20 | 3,039.0 |
| R | C10H21 | 0 | 0 | 0 | 155.0 |
| S | C12H25 | 5 | 1 | 5 | 682.0 |
| T | C18H37 | 0 | 10 | 0 | 857.0 |
| U | C20H21 | 5 | 1 | 10 | 994.0 |

Class 4

Imidazoline amines

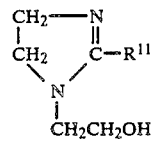

$R^{11}$ is alkyl having from 6 to 20 carbon atoms.

| Raw Material Example | $R^{11}$ | Molecular Weight |
|---|---|---|
| V | C7H15 | 186.0 |
| W | C11H23 | 242.0 |
| X | C17H35 | 326.0 |
| Y | C19H40 | 355.0 |
| Z | C6H13 | 172.0 |

NEUTRALIZATION

General Procedure

EXAMPLES 67-93

| Example Number | Phosphate Intermediate Example | Amine Reactant Example | Grams |
|---|---|---|---|
| 67 | 39 | A | 106.5 |
| 68 | 40 | B | 71.5 |
| 69 | 41 | C | 71.5 |
| 70 | 42 | D | 85.5 |
| 71 | 43 | E | 141.5 |
| 72 | 44 | F | 155.5 |
| 73 | 45 | G | 92.5 |
| 74 | 46 | H | 148.5 |
| 75 | 47 | I | 64.5 |
| 76 | 48 | J | 92.5 |
| 77 | 49 | K | 106.5 |
| 78 | 50 | L | 134.5 |
| 79 | 51 | M | 229.8 |
| 80 | 52 | N | 71.5 |
| 81 | 53 | O | 319.0 |
| 82 | 54 | P | 213.0 |
| 83 | 55 | Q | 3,039.0 |
| 84 | 56 | R | 155.0 |
| 85 | 57 | S | 682.0 |
| 86 | 58 | T | 857.0 |
| 87 | 59 | U | 994.0 |
| 88 | 60 | V | 186.0 |
| 89 | 61 | W | 242.0 |
| 90 | 62 | X | 326.0 |
| 91 | 63 | Y | 355.0 |
| 92 | 64 | Z | 172.0 |
| 93 | 65 | A | 213.0 |
| 94 | 66 | B | 143.0 |
| 95 | 53 | C | 143.0 |
| 96 | 54 | D | 171.0 |
| 97 | 55 | E | 283.0 |
| 98 | 56 | F | 311.0 |
| 99 | 57 | G | 185.0 |
| 100 | 58 | H | 297.0 |
| 101 | 59 | I | 129.0 |
| 102 | 60 | J | 185.0 |
| 103 | 61 | K | 213.0 |
| 104 | 61 | L | 269.0 |
| 105 | 63 | M | 325.0 |
| 106 | 64 | N | 143.0 |
| 107 | 39 | O | 159.5 |
| 108 | 40 | P | 106.5 |
| 109 | 41 | Q | 1,519.5 |
| 110 | 42 | R | 77.5 |
| 111 | 43 | S | 341.0 |
| 112 | 44 | T | 428.5 |
| 113 | 45 | U | 497.0 |
| 114 | 46 | V | 93.0 |
| 115 | 47 | W | 121.0 |
| 116 | 48 | X | 163.0 |
| 117 | 49 | Y | 177.5 |
| 118 | 50 | Z | 86.0 |

APPLICATIONS EXAMPLES

The compounds of the present invention produce a copious thick foam when diluted to 1% active in cylinder shake foam tests.

The compounds of the present invention are very mild to the skin, eyes and mucous membrane when applied at 10% active.

The compounds of the present invention are not toxic when tested in LD 50 tests.

All of these attributes make the compounds of the present invention candidates for use in personal care compositions.

What is claimed:

1. A silicone phosphate compound which conforms to the following structure;

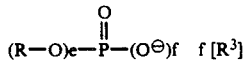

wherein
R is

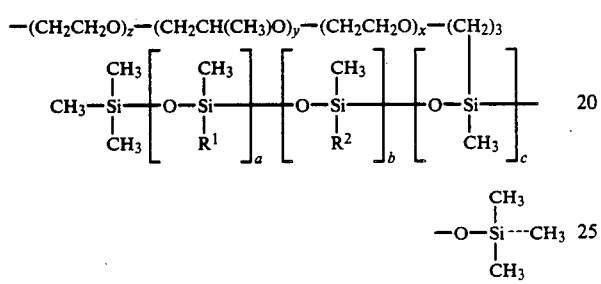

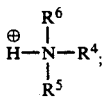

a is an integer from 0 to 200;
a is an integer from 0 to 200;
c is an integer from 1 to 200;
$R^1$ is selected from $-(CH_2)_n CH_3$ or phenyl;
n is an integer from 0 to 10;
$R^2$ is $-(CH_2)_3-(OCH_2CH_2)x-(OCH_2CH(CH_3))y-(OCH_2CH_2)z-OH$;
x, y and z are integers and are independently selected from 0 to 20;
e and f range from 1 to 2 with the proviso that e+f=3;
$R^3$ is selected from

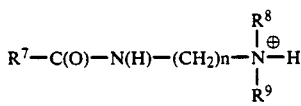

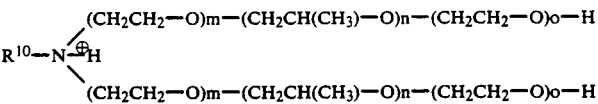

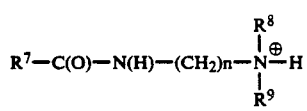

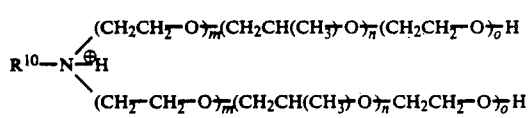

or

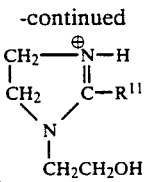

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are lower alkyl having from one to three carbon atoms;
$R^{10}$ is alkyl having from 6 to 20 carbon atoms;
$R^{11}$ is alkyl having from 6 to 20 carbon atoms;
m, n, and o are independently integers each ranging from 0 to 20.

2. A compound of claim 1 wherein;
$R^3$ is

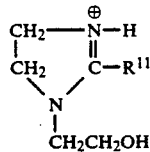

$R^4$ is alkyl having from 1 to 20 carbon atoms;
$R^5$ is alkyl having from 1 to 20 carbon atoms;
$R^6$ is alkyl having from 6 to 20 carbon atoms;

3. A compound of claim 1 wherein;
$R^3$ is $$R^7-C(O)-N(H)-(CH_2)n-\overset{R^8}{\underset{R^9}{N^\oplus}}-H$$

$R^7$ is alkyl having from 6 to 20 carbon atoms;
$R^8$ is alkyl having from 1 to 3 carbon atoms;
$R^9$ is alkyl having from 1 to 3 carbon atoms;

4. A compound of claim 1 wherein;
$R^3$ is $$R^{10}-N^{\oplus}H \begin{array}{l}(CH_2CH_2-O)m-(CH_2CH(CH_3)-O)n-(CH_2CH_2-O)o-H \\ (CH_2CH_2-O)m-(CH_2CH(CH_3)-O)n-(CH_2CH_2-O)o-H\end{array}$$

$R^{10}$ is alkyl having from 6 to 20 carbon atoms;
m, n, and o are independently integers each ranging from 0 to 20.

5. A compound of claim 1 wherein
$R^3$ is

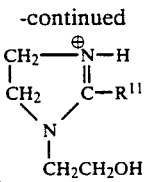

$R^{11}$ is alkyl having from 6 to 20 carbon atoms;

6. A compound of claim 1 wherein x, y and z are each zero.

7. A compound of claim 2 wherein x, y and z are each zero.

8. A compound of claim 3 wherein x, y and z are each zero.

9. A compound of claim 4 wherein x, y and z are each zero.

10. A process for conditioning fibers which comprises contacting the fiber with from 0.1% to 50% by weight of a silicone phosphate compound which conforms to the following structure;

$$(R-O)_e-\overset{O}{\underset{\|}{P}}-(O^{\ominus})_f \ f\ [R^3]$$

wherein
R is

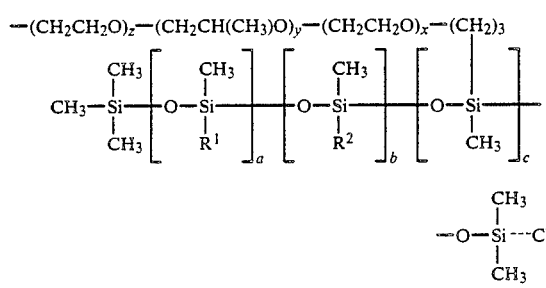

a is an integer from 0 to 200;
b is an integer from 0 to 200;
c is an integer from 1 to 200;
$R^1$ is selected from $-(CH_2)_nCH_3$ or phenyl;
n is an integer from 0 to 10;
$R^2$ is $-(CH_2)_3-(OCH_2CH_2)_x-(OCH_2CH(CH_3))_y-(OCH_2CH_2)_z-OH$;
x, y and z are integers and are independently selected from 0 to 20;
e and f range from 1 to 2 with the proviso that e+f=3;
$R^3$ is selected from $$\overset{\oplus}{H}-\underset{R^5}{\overset{R^6}{\underset{|}{\overset{|}{N}}}}-R^4;$$

$$R^7-C(O)-N(H)-(CH_2)_n-\overset{R^8}{\underset{R^9}{\overset{|}{\underset{|}{\overset{\oplus}{N}}}}}-H$$

$$R^{10}-\overset{(CH_2CH_2-O)_m(CH_2CH(CH_3)-O)_n(CH_2CH_2-O)_oH}{\underset{(CH_2CH_2-O)_m(CH_2CH(CH_3)-O)_n(CH_2CH_2-O)_oH}{N^{\oplus}H}}$$

or $$\underset{\underset{CH_2CH_2OH}{|}}{\overset{CH_2\quad\overset{\oplus}{N}-H}{\underset{CH_2\quad\overset{\|}{C}-R^{11}}{\diagdown\quad\diagup}}}$$

$R^4$ is alkyl having from 1 to 20 carbon atoms;
$R^5$ is alkyl having from 1 to 20 carbon atoms;
$R^6$ is alkyl having from 1 to 20 carbon atoms;
$R^7$ is alkyl having from 1 to 20 carbon atoms;
$R^8$ and $R^9$ are lower alkyl having from one to three carbon atoms;
$R^{10}$ is alkyl having from 6 to 20 carbon atoms;
$R^{11}$ is alkyl having from 6 to 20 carbon atoms;
m, n, and o are independently integers each ranging from 0 to 20.

11. A process of claim 10 wherein $R^3$ is $$\overset{\oplus}{H}-\underset{R^5}{\overset{R^6}{\underset{|}{\overset{|}{N}}}}-R^4;$$

$R^4$ is alkyl having from 1 to 20 carbon atoms;
$R^5$ is alkyl having from 1 to 20 carbon atoms;
$R^6$ is alkyl having from 6 to 20 carbon atoms;

12. A process of claim 10 wherein;
$R^3$ is $$R^7-C(O)-N(H)-(CH_2)_n-\overset{R^8}{\underset{R^9}{\overset{|}{\underset{|}{\overset{\oplus}{N}}}}}-H$$

$R^7$ is alkyl having from 6 to 20 carbon atoms;
$R^8$ is alkyl having from 1 to 3 carbon atoms;
$R^9$ is alkyl having from 1 to 3 carbon atoms;

13. A process of claim 10 wherein $R^3$ is $$R^{10}-\overset{(CH_2CH_2-O)_m-(CH_2CH(CH_3)-O)_n-(CH_2CH_2-O)_o-H}{\underset{(CH_2CH_2-O)_m-(CH_2CH(CH_3)-O)_n-(CH_2CH_2-O)_o-H}{N^{\oplus}H}}$$

$R^{10}$ is alkyl having from 6 to 20 carbon atoms;
m, n, and o are independently integers each ranging from 0 to 20.

14. A process of claim 10 wherein
$R^3$ is
$R^{11}$ is alkyl having from 6 to 20 carbon atoms;

15. A process of claim 10 wherein x, y and z are each zero.

16. A process of claim 11 wherein x, y and z are each zero.

17. A process of claim 12 wherein x, y and z are each zero.

18. A process of claim 13 wherein x, y and z are each zero.

* * * * *